(12) United States Patent
Kim et al.

(10) Patent No.: US 9,671,149 B2
(45) Date of Patent: Jun. 6, 2017

(54) REFRIGERATOR

(75) Inventors: Ji Hoon Kim, Gwangju (KR); Sung Cheol Kang, Gwangju (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 664 days.

(21) Appl. No.: 13/350,164

(22) Filed: Jan. 13, 2012

(65) Prior Publication Data

US 2012/0181911 A1 Jul. 19, 2012

(30) Foreign Application Priority Data

Jan. 17, 2011 (KR) .......................... 10-2011-0004386

(51) Int. Cl.
*F25B 43/04* (2006.01)
*F25D 17/04* (2006.01)
*A61L 2/14* (2006.01)

(52) U.S. Cl.
CPC .............. *F25D 17/042* (2013.01); *A61L 2/14* (2013.01); *F25D 2317/041* (2013.01)

(58) Field of Classification Search
CPC ..... F25D 17/042; F25D 2317/041; A61L 2/14
USPC ............................... 62/264, 78, 441; 361/231
See application file for complete search history.

(56) References Cited

U.S. PATENT DOCUMENTS

| | | | |
|---|---|---|---|
| 5,322,366 A * | 6/1994 | Revlett et al. | 312/405.1 |
| 6,443,056 B1 * | 9/2002 | Kiefer et al. | 99/475 |
| 7,854,900 B2 * | 12/2010 | Takeda et al. | 422/120 |
| 8,049,170 B2 * | 11/2011 | Sekoguchi et al. | 250/324 |
| 2004/0007000 A1 * | 1/2004 | Takeda et al. | 62/78 |
| 2004/0035128 A1 * | 2/2004 | Kaji et al. | 62/264 |
| 2005/0268623 A1 * | 12/2005 | Urakubo et al. | 62/78 |
| 2006/0263280 A1 * | 11/2006 | Ohtsuka et al. | 422/291 |
| 2007/0107452 A1 * | 5/2007 | Kim et al. | 62/264 |
| 2007/0163286 A1 * | 7/2007 | Lim | F25D 23/126 62/389 |
| 2008/0148743 A1 * | 6/2008 | On et al. | 62/78 |
| 2010/0071397 A1 * | 3/2010 | Takeda et al. | 62/264 |
| 2010/0223944 A1 * | 9/2010 | Tsujimoto et al. | 62/264 |
| 2012/0204581 A1 * | 8/2012 | Kang et al. | 62/78 |
| 2012/0300356 A1 * | 11/2012 | Katano | 361/231 |

FOREIGN PATENT DOCUMENTS

| | | |
|---|---|---|
| CN | 1875237 | 12/2006 |
| JP | 2001-263916 | 9/2001 |
| JP | 2002-90058 | 3/2002 |

(Continued)

OTHER PUBLICATIONS

Machine translation of WO 2010/024078 (Inoue et al).*

(Continued)

*Primary Examiner* — Larry Furdge
(74) *Attorney, Agent, or Firm* — Staas & Halsey LLP

(57) ABSTRACT

A refrigerator with a sterilization device. The sterilization device mounted at an upper surface of a storage chamber includes a housing formed, at a front surface thereof, with an ion outlet while being formed, at a base surface thereof, with an air inlet, an ion generating unit arranged in rear of the ion outlet to generate ions, a blast unit slantingly arranged at a position adjacent to the air inlet, and a guide portion formed to protrude at an upper surface of the housing which faces the blast unit, thereby enabling improvement in sterilization efficiency.

11 Claims, 7 Drawing Sheets

(56) References Cited

FOREIGN PATENT DOCUMENTS

| JP | 2002-130910 | 5/2002 |
|---|---|---|
| JP | 2003-42645 | 2/2003 |
| JP | 2009-30917 | 2/2009 |
| KR | 10-2006-0080024 | 7/2006 |
| WO | 2005/043063 A1 | 5/2005 |
| WO | 2010/024078 A1 | 3/2010 |

OTHER PUBLICATIONS

European Search Report dated Nov. 25, 2013 issued in corresponding European Patent Application 12150864.2.
Chinese Office Action issued Feb. 28, 2015 in corresponding Chinese Patent Application No. 201210006857.5.
European Office Action dated Jul. 13, 2016 from European Patent Application No. 12150864.2, 4 pages.
Chinese Notice of Allowance dated Jul. 12, 2016 from Chinese Patent Application No. 201210006857.5, 6 pages.
Korean Office Action dated Dec. 20, 2016 from Korean Patent Application No. 10-2011-0004386, 11 pages.

* cited by examiner

REFRIGERATOR

CROSS-REFERENCE TO RELATED APPLICATIONS

This application claims the priority benefit of Korean Patent Application No. 10-2011-0004386 filed on Jan. 17, 2011 in the Korean Intellectual Property Office, the disclosure of which is incorporated herein by reference.

BACKGROUND

1. Field

Embodiments relate to a refrigerator with a sterilization device for sterilization and deodorization.

2. Description of the Related Art

In general, a refrigerator is used to preserve food, etc. in a fresh state for a long time using cold air produced by heat exchange with an evaporator. Such a refrigerator includes a storage chamber composed of a refrigerating chamber and a freezing chamber. Also, the storage chamber is provided, at a rear side thereof, with an evaporator to generate cold air and a cold air supply device composed of a duct, a fan, etc. in order to circulate cold air generated by the evaporator in the storage chamber. The cold air is supplied to the storage chamber through the cold air supply device, and is then circulated so as to maintain the storage chamber at a proper temperature.

Meanwhile, since various kinds of agricultural and livestock food such as eggs, vegetables, fruits, meats, etc., which are stored in the storage chamber, are delivered to a user via several distribution channels after yielded from local producers, many harmful germs exist in the food itself. For these reasons, a refrigerator with a sterilization device and a deodorization device to remove germs and odors has been proposed recently.

SUMMARY

Therefore, it is an aspect of one or more embodiments to provide a refrigerator with a sterilization device capable of achieving improvement in efficiency of sterilization performance.

It is another aspect of one or more embodiments to provide a refrigerator with a sterilization device having improved ease of use.

Additional aspects of one or more embodiments will be set forth in part in the description which follows and, in part, will be apparent from the description, or may be learned by practice.

In accordance with an aspect of one or more embodiments, a refrigerator includes a main body having a storage chamber, a door mounted at the main body so as to open and close the storage chamber, and a sterilization device mounted at an upper surface of the storage chamber in order to sterilize and deodorize an interior of the storage chamber, wherein the sterilization device includes a housing formed, at a front surface thereof, with an ion outlet while being formed, at a base surface thereof, with an air inlet, a blast unit mounted within the housing so as to suction air within the storage chamber to the air inlet, an ion generating unit mounted between the ion outlet and the blast unit so as to generate ions through supply of the air suctioned by the blast unit, and a guide portion formed at an inner side of the housing so as to guide the air discharged from the blast unit toward the ion generating unit.

The sterilization device may be mounted in an attachable and detachable manner.

The guide portion may have a slanted surface which protrudes from the housing to slant downwards toward the ion outlet.

The blast unit may be arranged within the housing to slant downwards toward the ion outlet.

The housing may further include a shield portion which encases a circumference of the blast unit except for an ion outlet side.

The sterilization device may further include a light emitting portion which displays an operation state of the sterilization device and a light penetrating member which transfers light emitted from the light emitting portion toward the ion outlet.

The sterilization device may further include a deodorization filter to deodorize the air suctioned through the air inlet.

The refrigerator may further include a seizing portion provided at the upper surface of the storage chamber and a binding portion provided at the housing to allow the seizing portion to be coupled and seized, wherein the seizing portion and the binding portion may be provided so as to be bound by contact therebetween during movement of the sterilization device along an upper wall of the storage chamber.

The storage chamber may be provided, at the upper surface thereof, with a sterilization device mounting portion which is concavely formed upwards as a shape corresponding to the sterilization device, and the sterilization device may be attachably mounted at the sterilization device mounting portion.

The refrigerator may further include a door operation sensing portion to detect an opening and closing state of the door and a control unit to control operation of the blast unit and ion generating unit depending on a signal detected from the door operation sensing portion.

The sterilization device may further include a drive circuit board which is electrically connected with the blast unit and the ion generating unit, and the drive circuit board may turn ON/OFF the operation of the blast unit and ion generating unit depending on a control signal of the control unit.

The refrigerator may further include a cold air circulating fan to circulate cold air which cools the storage chamber and a control unit to control operation of the blast unit and ion generating unit depending on an operation signal of the cold air circulating fan.

In accordance with another aspect of one or more embodiments, a refrigerator includes a storage chamber, a door to open and close the storage chamber, a door operation sensing portion to detect opening or closing of the door, a cold air circulating fan to forcibly circulate cold air of the storage chamber, a sterilization device which includes a housing, an ion outlet formed at a front surface of the housing, an ion generating unit arranged in rear of the ion outlet to generate ions, an air inlet formed at a base surface of the housing, a blast unit arranged at a position adjacent to the air inlet, and a guide portion formed at an upper surface of the housing to guide air discharged from the blast unit toward the ion outlet, and a control unit to control operation of the sterilization device.

The control unit may determine the opening or closing of the door depending on a signal detected from the door operation sensing portion to operate the sterilization device.

The control unit may stop the operation of the sterilization device when the door is opened, whereas operate the sterilization device for a predetermined time when the door is closed.

The sterilization device may further include a light emitting portion which displays an operation state of the sterilization device, and the control unit may determine the opening or closing of the door to operate the light emitting portion.

The control unit may turn ON the light emitting portion when the door is opened, whereas turn OFF the light emitting portion when the door is closed.

The control unit may determine whether the cold air circulating fan is operated or not to operate the sterilization device.

The control unit may operate the sterilization device for a predetermined time when the cold air circulating fan is operated.

In accordance with a further aspect of one or more embodiments, a refrigerator includes a storage chamber, an input portion to input a setting temperature within the storage chamber, a temperature sensing portion to detect a temperature within the storage chamber, a sterilization device mounted at an upper surface of the storage chamber for sterilization and deodorization of the storage chamber, the sterilization device including a housing, an ion outlet formed at a front surface of the housing, an ion generating unit arranged in rear of the ion outlet to generate ions, an air inlet formed at a base surface of the housing, a blast unit arranged at a position adjacent to the air inlet, and a guide portion formed at an upper surface of the housing so as to guide air discharged from the blast unit to the ion outlet, and a control unit to compare the setting temperature input through the input portion with a temperature detected by the temperature sensing portion and to control operation of the sterilization device.

When the setting temperature is lower than the detected temperature, the control unit may operate the blast unit and the ion generating unit.

BRIEF DESCRIPTION OF THE DRAWINGS

These and/or other aspects of the invention will become apparent and more readily appreciated from the following description of embodiments, taken in conjunction with the accompanying drawings of which.

DETAILED DESCRIPTION

Figure 1:
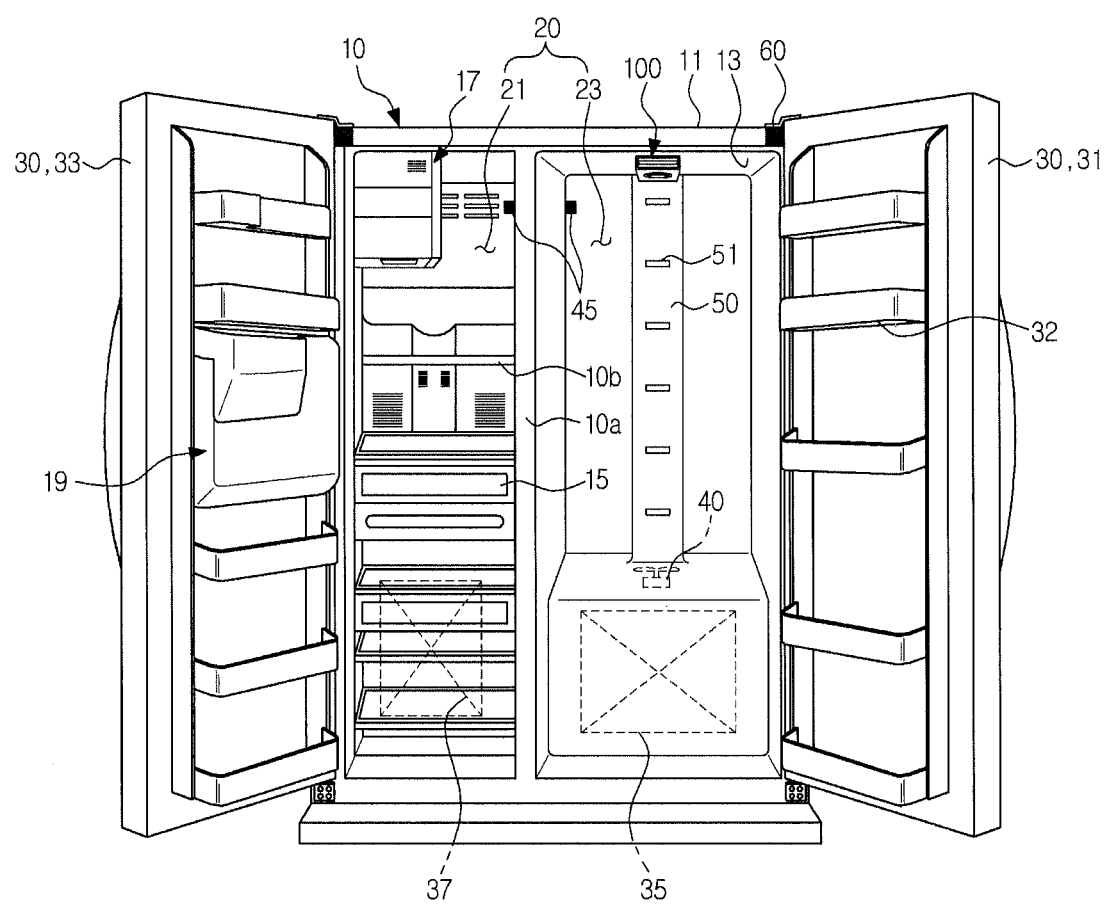
FIG. 1 is a view illustrating a state of opening a door of a refrigerator according to an embodiment.

Reference will now be made in detail to embodiments, examples of which are illustrated in the accompanying drawings, wherein like reference numerals refer to like elements throughout.

FIG. 1 is a view illustrating a state of opening a door of a refrigerator according to an embodiment.

As shown in FIG. 1, the refrigerator according to an embodiment may include a main body 10 defining an external appearance thereof while having a storage chamber 20 and a door 30 mounted at the main body 10 to open and close the storage chamber 20.

The main body 10 may include an outer case 11 defining an external appearance thereof, an inner case 13 spaced apart from the outer case 11 by a predetermined clearance to define the storage chamber 20, and an insulation material 12 (see FIG. 2) foamed between the outer case 11 and the inner case 13.

The storage chamber 20 may include a refrigerating chamber 23 and a freezing chamber 21 which are divided by a vertical partition wall 10a. The door may includes a refrigerating chamber door 31 and a freezing chamber door 33 to open and close the refrigerating chamber 23 and the freezing chamber 21, respectively.

A plurality of shelves 10b on which food is placed may be arranged to be spaced apart in upward and downward directions at the refrigerating chamber 23 and the freezing chamber 21. The refrigerating chamber 23 and the freezing chamber 21 may be provided with a plurality of storage drawers 15 which are extractably installed to store food.

The freezing chamber 21 may be equipped, at one side of an upper portion thereof, with an ice maker 17 to make ice cubes, and the freezing chamber door 33 may be equipped with a dispenser 19 from which ice cubes made in the ice maker 17 are discharged. The dispenser 19 is used to extract ice cubes or water without opening the door 30.

The refrigerating chamber 23 and the freezing chamber 21 are installed, at rear sides thereof, with a refrigerating chamber evaporator 35 and a freezing chamber evaporator 37 which generate cold air to cool the refrigerating chamber 23 and the freezing chamber 21, respectively. The cold air generated in the refrigerating chamber evaporator 35 and the freezing chamber evaporator 37 is discharged to the refrigerating chamber 23 and the freezing chamber 21 through cold air supply devices, respectively.

Each of the cold air supply devices is provided at the refrigerating chamber 23 and the freezing chamber 21. However, since the cold air supply devices have a symmetric structure to each other, only the cold air supply device installed at the refrigerating chamber 23 will be described below.

The cold air supply device may include a cold air circulating fan 40 to forcibly circulate cold air generated in the refrigerating chamber evaporator 35 and a cold air duct 50 through which the cold air blown by the cold air circulating fan 40 flows.

The cold air duct 50 may have a plurality of cold air outlet holes 51 to discharge cold air to the refrigerating chamber 23, and the cold air outlet holes 51 are arranged to be spaced apart in upward and downward directions. Furthermore, the cold air duct 50 may have a cold air inlet hole (not shown) to allow the cold air which cools the refrigerating chamber 23 to be suctioned and returned to the refrigerating chamber evaporator 35. In addition, the cold air duct 50 may be provided therein with a damper (not shown) to regulate an amount of cold air discharged to the refrigerating chamber 23.

In accordance with such a configuration, cold air generated by heat exchange in the refrigerating chamber evaporator 35 is discharged to the refrigerating chamber 23 by blast force of the cold air circulating fan 40 through the cold air outlet holes 51 formed at the cold air duct 50 so as to cool the refrigerating chamber 23. Subsequently, the cold air which cools the refrigerating chamber 23 is again returned to the refrigerating chamber evaporator 35 through the cold air inlet hole, thereby being forcibly circulated.

Each of the refrigerating chamber 23 and the freezing chamber 21 may be provided with a temperature sensing portion 45 to detect an interior temperature thereof.

The refrigerating chamber 23 may be mounted, at an upper surface thereof, with a sterilization device 100 to sterilize and deodorize food stored in the refrigerating chamber 23. The sterilization device 100 is used to suction air of the refrigerating chamber 23 so as to generate ions and supply the refrigerating chamber 23 with the generated ions so as to sterilize harmful germs such as viruses, bacteria, and mold contained in the air. Such a sterilization device 100 will be described in detail below.

Each of the refrigerating chamber door 31 and the freezing chamber door 33 is provided, at an inner surface thereof, with door guards 32 to store food of a small size, bottles or the like. The refrigerating chamber door 31 and the freezing chamber door 33 are pivotably coupled to opposite sides of the main body 10 to open and close the refrigerating chamber 23 and the freezing chamber 21, respectively.

The door 30 may be provided with a button to allow a user to put operation signals (for example, a setting temperature, etc.) of the refrigerator, and an input portion 42 (see FIG. 7) composed of a display and the like to display an operation state and the like of the refrigerator. The operation signals selected from the input portion 42 are transmitted to a control unit 70 (see FIG. 7) to control operation of the refrigerator over all.

The main body 10 may be provided, at one side of an upper portion thereof, with a door operation sensing portion 60 to selectively come into contact with the door 30 during opening and closing of the door 30 so as to detect whether the door 30 is opened or not.

The door operation sensing portion 60 is electrically connected with the control unit 70, and a signal detected in the door operation sensing portion 60 is transmitted to the control unit 70.

The control unit 70 may be comprised of a microprocessor, a microcontroller and the like which have a central processing unit (CPU), wherein the CPU executes a plurality of computer commands to control overall operation of the refrigerator including components such as a compressor (not shown) and the like which configure a refrigeration cycle, the cold air supply devices, the sterilization device 100 and the like, or to perform various types of control operation. Also, the control unit 70 may include a memory device such as a random access memory (RAM), a read only memory (ROM) and the like.

Figure 2:
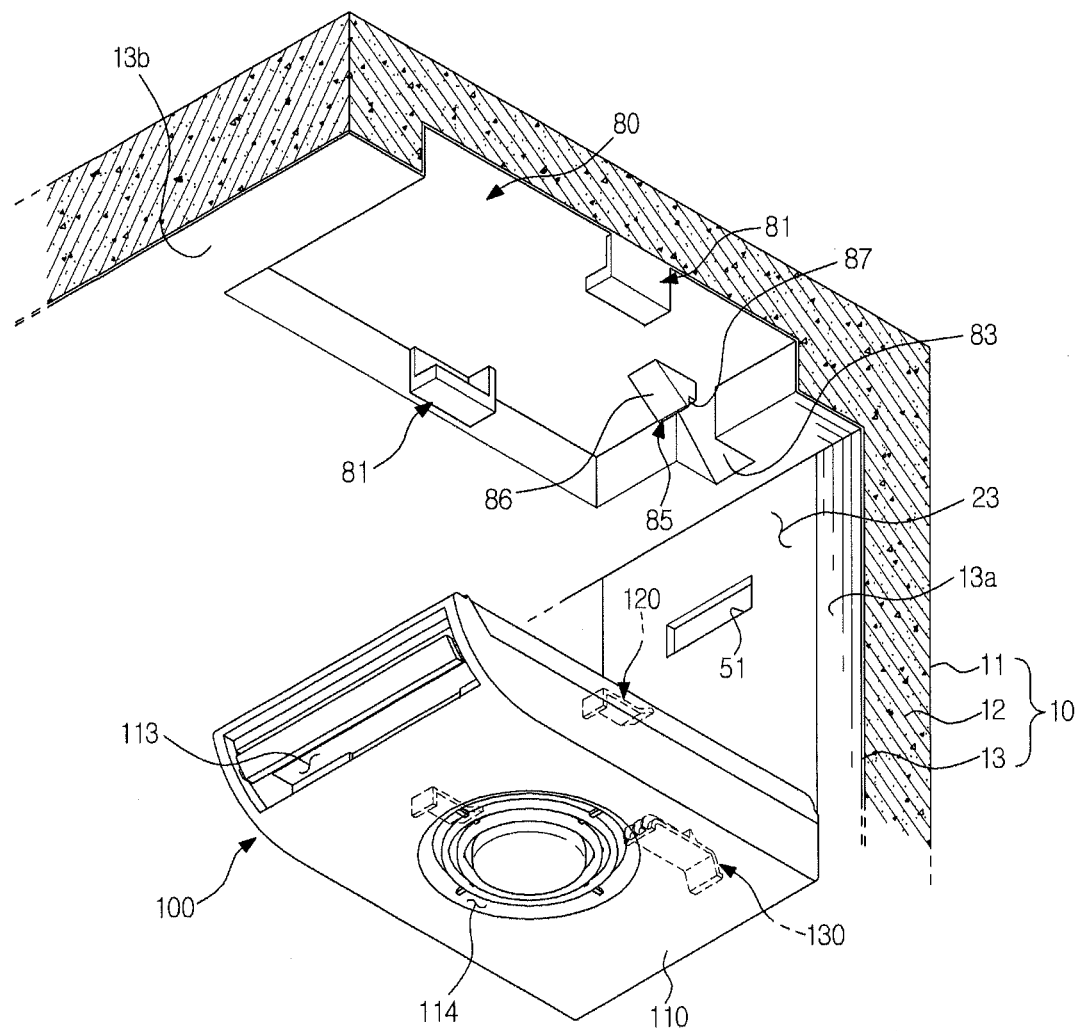
FIG. 2 is a view illustrating a portion at which a sterilization device is mounted in a refrigerating chamber according to an embodiment.
Figure 3:
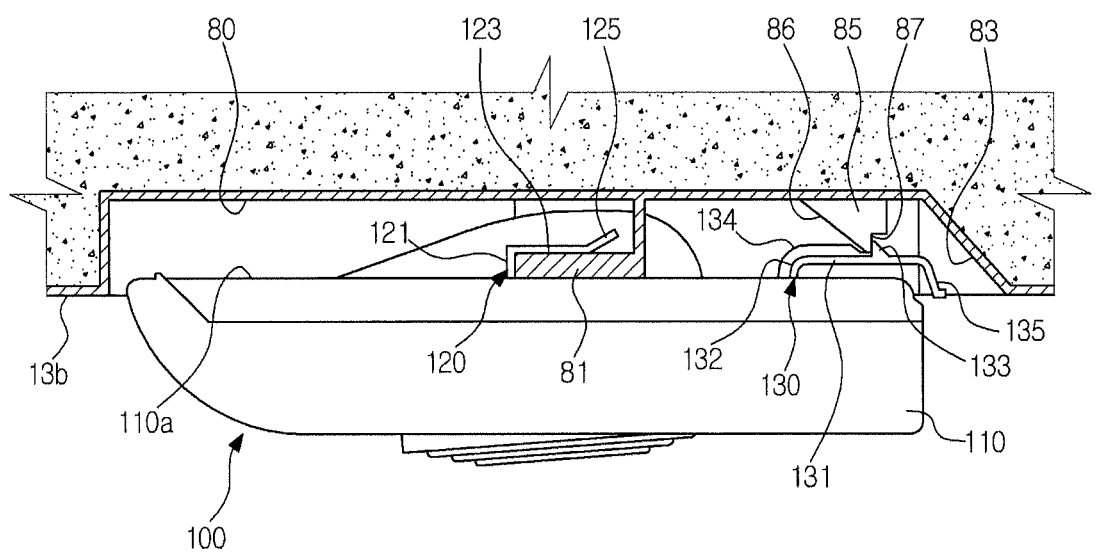
FIG. 3 is a coupled sectional view illustrating a mounted state of the sterilization device in the refrigerating chamber according to an embodiment.

FIG. 2 is a view illustrating a portion at which the sterilization device is mounted in the refrigerating chamber according to an embodiment. FIG. 3 is a coupled sectional view illustrating a mounted state of the sterilization device in the refrigerating chamber according to an embodiment.

As shown in FIGS. 2 and 3, a sterilization device mounting portion 80 may be formed at a rear upper side of the inner case 13 defining the refrigerating chamber 23. The sterilization device mounting portion 80 is formed to be recessed by a predetermined depth.

The sterilization device 100 includes a housing 110 of a substantially rectangular shape, and the housing 110 may be a slim shape formed to be long in length compared with a width.

The sterilization device 100 is accommodated in the sterilization device mounting portion 80 of a concave shape, thereby reducing an area occupied in a space of the refrigerating chamber 23 to increase an effective capacity of the refrigerating chamber 23.

The sterilization device mounting portion 80 may be formed at a rear side of the upper surface of the refrigerating chamber 23 which is placed adjacent to the cold air outlet holes 51 so that cold air is discharged from the cold air outlet holes 51 formed at the rear side of the refrigerating chamber 23 and is easily introduced into the sterilization device 100.

Also, the sterilization device 100 may be attachably mounted at the sterilization device mounting portion 80 so as to enable mounting and separation of the sterilization device 100 by simple operation.

In order to achieve this, the sterilization device mounting portion 80 may have a shape corresponding to the housing 110 of the sterilization device 100. In addition, the sterilization device mounting portion 80 may be formed, at opposite side walls thereof, with support ribs 81 which protrude and extend in front and rear directions to support the sterilization device 100. Furthermore, the sterilization device mounting portion 80 may be provided, at a rear side of an upper surface thereof, with a seizing portion 85 to restrict movement of the sterilization device 100 in a front direction when the sterilization device 100 moves to slide toward a rear wall 13a of the refrigerating chamber 23 in a state of being supported by the support ribs 81 and is mounted at the sterilization device mounting portion 80.

The housing 110 of the sterilization device 100 may be provided, at opposite sides of an upper surface thereof, with insertion ribs 120 to allow the respective support ribs 81 formed at the sterilization device mounting portion 80 to be inserted and supported. Also, the housing 110 may be provided, at a rear side of the upper portion thereof, with a binding portion 130 which comes into contact with the seizing portion 85 to elastically deformed during sliding movement of the housing 110 along the support ribs 81, and is then bound to the seizing portion 85.

The seizing portion 85 may be formed to extend from the upper surface of the sterilization device mounting portion 80 in a downward direction, and may be a triangular sectional shape having a slanted surface 86 and a vertical surface 87. The slanted surface 86 presses the binding portion 130 so that the binding portion 130 is guided to smoothly enter and is elastically deformed at the same time. On the other hand, the vertical surface 87 functions to be bound to the binding portion 130 when the binding portion 130 is elastically deformed and is then restored.

The binding portion 130 may include an elastically deformable bent plate 131 which protrudes from the upper surface 110a of the housing 110 and bendably extends toward the rear wall 13a of the refrigerating chamber 23. The bent plate 131 may be formed, at an upper surface thereof, with a hook portion 133 which protrudes to be coupled with the vertical surface 87 of the seizing portion 85 in a hook fashion while being formed, at an end thereof, with a push portion 135 which is formed to extend in the downward direction and have a predetermined shape.

The bent plate 131 is arranged to be elastically deformed in upward and downward directions about a bending portion 132, and the bending portion 132 provides elastic force which presses the hook portion 133 in an upward direction. In addition, the bent plate 131 may be provided, at the upper surface thereof, with reinforcement ribs 134 to reinforce the bending portion 132.

When a user separates the sterilization device 100 from the sterilization device mounting portion 80, a user presses the push portion 135 which performs function to release binding between the hook portion 133 and the vertical surface 87 of the seizing portion 85.

The sterilization device mounting portion 80 may be formed, at a rear side thereof facing the seizing portion 85, with a finger insertion groove 83 cut such that a user may easily press the push portion 135.

Each insertion rib 120 may have a vertical portion 121 which vertically extends from the upper surface 110a of the housing 110 and a horizontal portion 123 which is bent from an end of the vertical portion 121 to extend in a horizontal direction, in order to form a groove to insert the corresponding support rib 81. Also, the insertion rib 120 may have a slanted portion 125 which is upwardly bent from an end of the horizontal portion 123 so as to enable the support rib 81 to smoothly enter the insertion rib 120.

In accordance with such a configuration, the sterilization device 100 of an embodiment is attachably provided at the upper surface 13b of the refrigerating chamber 23 without using a separation tool, thereby enabling mounting and separation thereof by a simple fashion. Furthermore, the sterilization device 100 is mounted at the sterilization device mounting portion 80 of the concave shape, thereby reducing an invalid space of the refrigerating chamber 23. As a result, capacity efficiency at the refrigerating chamber 23 is improved.

Figure 4:
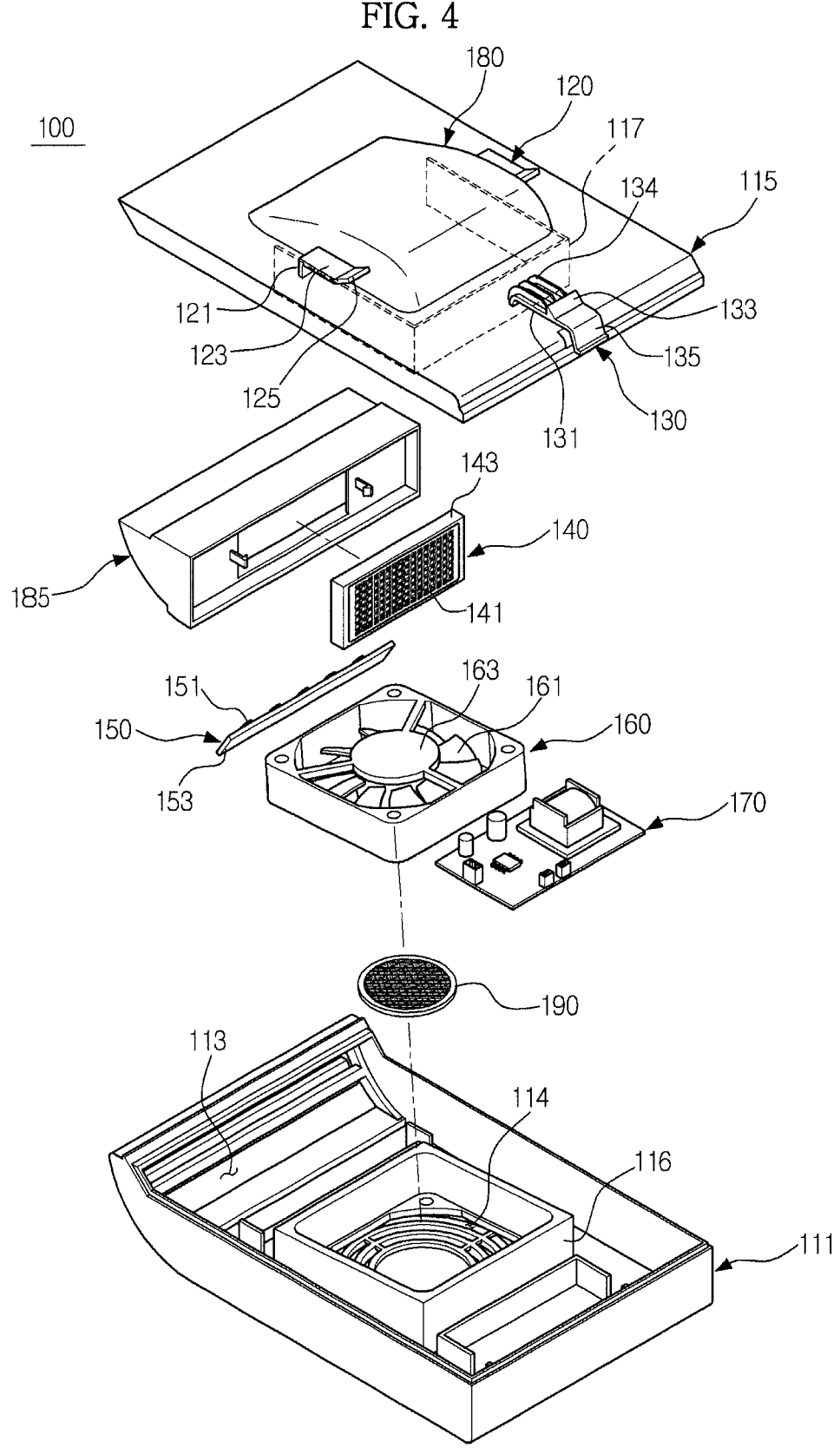
FIG. 4 is an exploded perspective view illustrating the sterilization device according to an embodiment.
Figure 5:
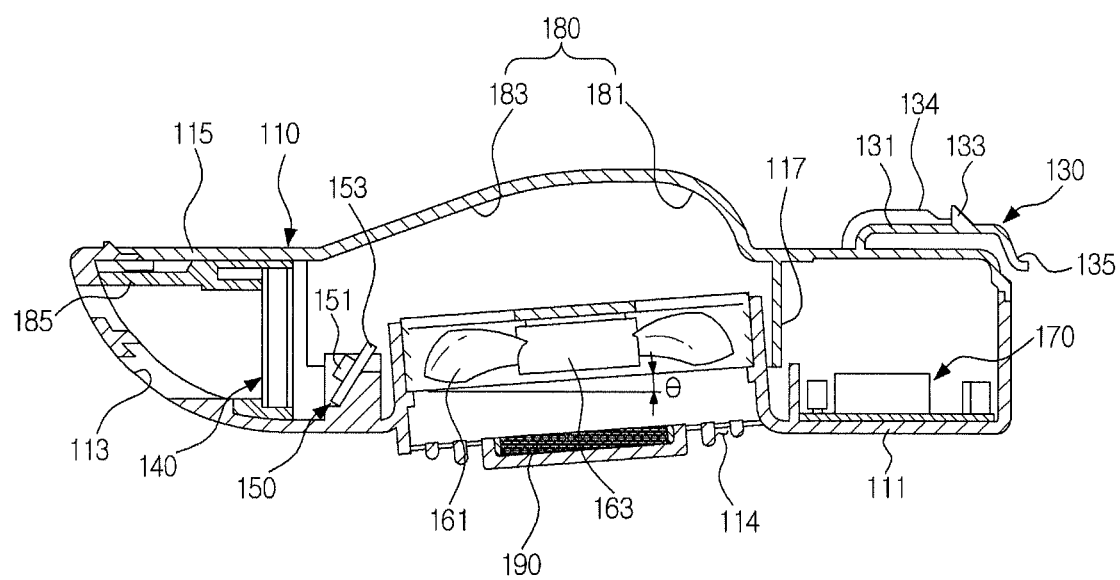
FIG. 5 is a coupled sectional view of the sterilization device illustrated in FIG. 4.

Hereinafter, the sterilization device according to an embodiment will be described. FIG. 4 is an exploded perspective view illustrating the sterilization device according to an embodiment. FIG. 5 is a coupled sectional view of the sterilization device illustrated in FIG. 4.

The sterilization device 100 of an embodiment includes the housing 110 which has an upper cover 115 and a lower cover 111 coupled to each other. The housing 110 is equipped with principal components for sterilization therein.

When the upper cover 115 and the lower cover 111 are coupled, the housing 110 has a substantially rectangular shape. The housing 110 may be formed, at a front surface thereof, with ion outlets 113 opened in a width direction while being formed, at a base surface thereof, with air inlets 114 to introduce outdoor air.

An ion generating unit 140 may be provided in rear of the ion outlets 113 in order to generate ions. The ion generating unit 140 is used as a device to generate ions by discharging high voltage, and may include an electrode portion 141 for discharge and an insulation member 143 to encase a circumference of the electrode portion 141.

The ion generating unit 140 is used to apply high voltage to the electrode portion 141 so as to ionize ambient air by discharge of the electrode portion 141.

The ions generated by the ion generating unit 140 sterilize harmful germs contained in the air within the refrigerating chamber 23 or remove foul odors. In an embodiment, although vertically arranged in the housing 110, the ion generating unit 140 may be slantingly arranged to correspond to the ion outlets 113 so as to reduce passage resistance of the discharged air.

A light penetrating member 185 made of a transparent material is mounted in the inside periphery of the ion outlets 113. The light penetrating member 185 allows beams emitted by a light emitting portion 150 arranged at a rear side thereof to be emitted to the outside through the ion outlets 113 side.

The light emitting portion 150 may include a plurality of light emitting diodes (LEDs) 151 arranged at a printed circuit board 153. Such a light emitting portion 150 functions to notify whether or not the sterilization device 100 is operated. Since light emitted from the light emitting portion 150 is transferred to the outside through the light penetrating member 185, the sterilization device 100 may have subdued lighting effects, and thus visibility is improved.

The lower cover 111 may be provided, at the inside thereof adjacent to the air inlets 114, with a blast unit mounting portion 116 at which a blast unit 160 is mounted in order to provide suction force to suction outdoor air through the air inlets 114.

The blast unit 160 suctions air outside the sterilization device 100 to supply the air toward the ion generating unit 140, and may include a fan 161 rotated by rotational force of a motor 163.

The blast unit 160 may be slantingly arranged at the blast unit mounting portion 116 so as to, allowing for flow of cold air discharged to cool the refrigerating chamber 23, smoothly suction the discharged cold air.

That is, blast unit 160 may be arranged to slant with respect to the horizontal direction (extending direction of the upper surface of the refrigerating chamber) at a predetermined angle e, for example, to slant downwards as approaching toward the ion outlets 113. This is to arrange the blast unit 160 so as to considerably accord with a discharge direction of the cold air discharged from the cold air outlet holes 51 which are formed at the rear wall 13a of the refrigerating chamber 23, in order to attain increase in flow and velocity of air introduced from the air inlets 114.

The upper cover 115 may include, at a position thereof facing a discharge portion of the blast unit 160, a guide portion 180 to protrude outwards and guide air discharged from the blast unit 160.

The guide portion 180 guides air so that the air discharged from the blast unit 160 is smoothly discharged toward the ion outlets 113. The guide portion 180 may include a curved surface 181 having predetermined curvature so as to reduce passage resistance of the discharged air, and a slanted surface 183 formed to slant downwards toward the ion outlets 113 so as to accelerate air discharged to the ion outlets 113.

The guide portion 180 may be provided, at an outer periphery thereof, with a shield portion 117 which extends downwards from the upper cover 115 and encases a circumference of the blast unit 160 in order to prevent flow loss of air discharged from the blast unit 160.

The shield portion 117 is opened at a front surface thereof so that air discharged from the blast unit 160 is transferred toward the ion outlets 113. Also, the shield portion 117 is blocked at side and rear surfaces thereof to prevent the discharged air from leaking outwards.

The air inlets 114 may be arranged in parallel with a suction direction of air by the blast unit 160 so as to reduce passage resistance of air suctioned from the blast unit 160 which is slantingly arranged.

Meanwhile, in order to enhance deodorization performance to remove foul odors contained in the air which is suctioned by the blast unit 160, a deodorization filter 190 made of a porous material is further included between the blast unit 160 and the air inlets 114 so as to adsorb odor particles contained in the air.

Figure 6:
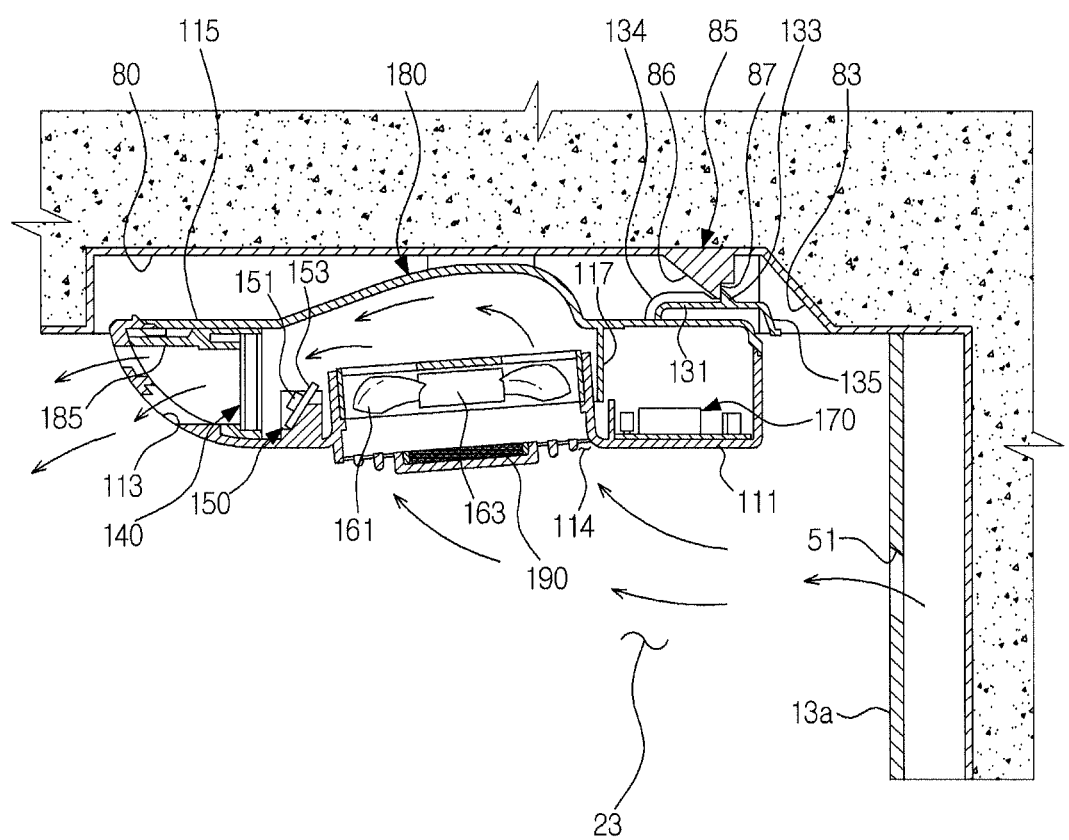
FIG. 6 is a view illustrating an ion discharge route of the sterilization device according to an embodiment.

In accordance with such a configuration, cold air discharged from the cold air outlet holes 51 formed at the rear wall 13a of the refrigerating chamber 23 is introduced through the air inlets 114 by suction force of the blast unit 160 to be discharged upwards, and subsequently the discharged cold air is guided by the guide portion 180 to be discharged to the refrigerating chamber 23 through the ion outlets 113 together with ions generated by the ion generating unit 140, as shown in FIG. 6.

Thus, the cold air containing ions discharged from the sterilization device 100 may reduce loss of air flow and air velocity. Consequently, since the cold air containing ions is diffused throughout the refrigerating chamber 23, sterilization and deodorization performance may be improved.

That is, the sterilization device 100 of an embodiment allows cold air discharged from the cold air outlet holes 51 to be rapidly introduced, and at the same time velocity of cold air discharged through the ion outlets 113 to be accelerated. Consequently, ions generated by the ion generating unit 140 may be diffused up to a distant location of the refrigerating chamber 23.

Meanwhile, the housing 110 may be provided therein with a drive circuit board 170 electrically connected to drive the blast unit 160, the ion generating unit 140, and the light emitting portion 150.

The drive circuit board 170 is electrically connected with the control unit 70 to receive operation signals of the respective blast unit 160, ion generating unit 140, and light emitting portion 150 from the control unit 70, and to respectively operate electric components of the sterilization 100 through supply of power.

Figure 7:
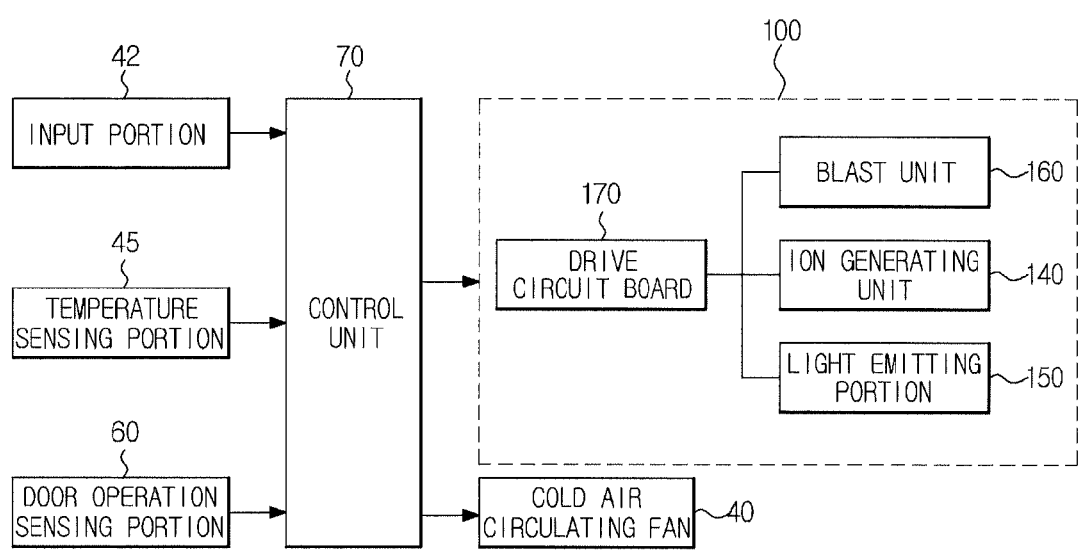
FIG. 7 is a block diagram illustrating a configuration to control operation of the refrigerator according to an embodiment.

Hereinafter, the operation of the refrigerator according to an embodiment will be described. FIG. 7 is a block diagram illustrating a configuration to control the operation of the refrigerator according to an embodiment.

As shown in FIG. 7, the block diagram to control the operation of the refrigerator may be comprised of the input portion 42, the temperature sensing portion 45, the door operation sensing portion 60, the control unit 70, the cold air circulating fan 40, and the sterilization device 100. The sterilization device 100 may be comprised of the drive circuit board 170, the blast unit 160, the ion generating unit 140, and the light emitting portion 150.

The input portion 42 is electrically connected with the control unit 70 so that the operation signals such as the setting temperature of the refrigerator and the like which are input through the input portion 42 are transmitted to the control unit 70 and stored in the memory device.

The temperature sensing portion 45 is provided at one side of the storage chamber 20 so as to detect an interior temperature of the storage chamber 20 and then transmit a signal detected therefrom to the control unit 70 which is electrically connected with the temperature sensing portion 45.

The control unit 70 compares the setting temperature which is input through the input portion 42 with a temperature transferred from the temperature sensing portion 45 so as to drive the cold air circulating fan 40 or transmit the corresponding operation signal to the sterilization device 100, thereby allowing cold air to be supplied depending on the setting temperature.

When the cold air circulating fan 40 is driven, the cold air generated in the refrigerating chamber evaporator 35 is discharged to the cold air outlet holes 51 via the cold air duct 50 so as to be supplied to the storage chamber 20.

The door operation sensing portion 60 detects opening or closing of the refrigerating chamber door 31 and then transmits a signal detected therefrom to the control unit 70.

The drive circuit board 170 is electrically connected with the control unit 70. Furthermore, the drive circuit board 170 is electrically connected with the control unit 70 so as to control operation of the blast unit 160, ion generating unit 140, and light emitting portion 150 depending on control signals of the control unit 70, respectively.

In addition, the control unit 70 analyses a signal detected from the door operation sensing portion 60 to determine the opening or closing of the refrigerating chamber door 31, and then transmits the corresponding operation signal to the drive circuit board 170 depending on the opening or closing of the refrigerating chamber door 31.

Hereinafter, a control method of the refrigerator according to an embodiment will be described.

In the refrigerator of an embodiment, operation of the sterilization device 100 may be controlled depending on the opening or closing of the door 30, or depending on a difference between the setting temperature input through the input portion 42 and the temperature of the storage chamber 20 detected by the temperature sensing portion 45. The control method of the refrigerator will be described based on operation states of the refrigerating chamber 23 and refrigerating chamber door 31 below.

First, as regards to the operation of the sterilization device 100 according to the opening or closing of the refrigerating chamber door 31, the control unit 70 receives the signal detected from the door operation sensing portion 60 which detects the opening or closing of the refrigerating chamber door 31 to determine whether the refrigerating chamber door 31 is opened or not.

When it is determined that the refrigerating chamber door 31 is opened, the control unit 70 controls the drive circuit board 170 of the sterilization device 100 to recognize visibility and normal operation of the sterilization device 100. Consequently, the control unit 70 turns ON the power of the light emitting portion 150 and simultaneously stops the operation of the blast unit 160 and ion generating unit 140 so as to prevent energy loss due to discharge of cold air.

On the other hand, when it is determined that the refrigerating chamber door 31 is closed, the control unit 70 turns OFF the power of the light emitting portion 150 and simultaneously operates the blast unit 160 and the ion generating unit 140 to sterilize and deodorize the refrigerating chamber 23.

In this case, the control unit 70 may continuously operate the blast unit 160 and the ion generating unit 140. However, the control unit 70 may control the blast unit 160 and the ion generating unit 140 so that the blast unit 160 and the ion generating unit 140 are operated only for a determined time or intermittently operated in order to reduce energy consumption.

Hereinafter, the operation of the sterilization device 100 according to the setting temperature through the input portion 42 will be described.

First, when a user inputs the temperature suitable for storage of food through the input portion 42, the input setting temperature is transferred to the control unit 70 and stored in the memory device of the control unit 70. Also, the control unit 70 receives the signal detected by the temperature sensing portion 45 provided at the refrigerating chamber 23 to compare the setting temperature with the detected temperature. In this case, when the setting temperature is lower than the detected temperature, the control unit 70 operates the cold air circulating fan 40 so as to supply the refrigerating chamber 23 with the cold air generated by heat exchange in the refrigerating chamber evaporator 35, and simultaneously operates the blast unit 160 and the ion generating unit 140.

Accordingly, the cold air discharged to the refrigerating chamber 23 is partially introduced into the sterilization device 100, and is then diffused evenly throughout the refrigerating chamber 23 together with ions generated by the ion generating unit 140, thereby sterilizing and deodorizing the interior of the refrigerating chamber 23. In such a case, the control unit 70 may also control the blast unit 160 and the ion generating unit 140 so that the blast unit 160 and the ion generating unit 140 are operated only for a determined time, continuously operated, or intermittently operated.

That is, when the setting temperature input through the input portion 42 is lower than the temperature detected by the temperature sensing portion 45, the control unit 70 operates the blast unit 160 and the ion generating unit 140. On the other hand, when the input setting temperature is higher than the detected temperature, the control unit 70 stops the operation of the blast unit 160 and ion generating unit 140.

Meanwhile, the control unit 70 may control the operation of the blast unit 160 and ion generating unit 140 depending on whether the cold air circulating fan 40 is operated or not, independent of controlling the blast unit 160 and the ion generating unit 140 depending on the difference between the setting temperature and the detected temperature.

That is, when the cold air circulating fan 40 is operated, the control unit 70 may operate the blast unit 160 and the ion generating unit 140, whereas when the cold air circulating fan 40 is not operated, the control unit 70 may stop the blast unit 160 and the ion generating unit 140. In such a case, the cold air circulating fan 40 may be controlled so as to be operated only for a determined time, continuously or intermittently operated.

As is apparent from the above description, the refrigerator according to an embodiment may evenly diffuse ions generated from the sterilization device throughout the storage chamber, thereby enabling improvement in sterilization and deodorization performance.

Also, in accordance with the refrigerator of an embodiment, the sterilization device may be mounted and separated in a simple way, thereby improving ease of use.

Although embodiments have been shown and described, it would be appreciated by those skilled in the art that changes may be made in embodiments without departing from the principles and spirit, the scope of which is defined in the claims and their equivalents.

What is claimed is:

1. A refrigerator comprising:
   a main body having a storage chamber;
   a door mounted at the main body so as to open and close the storage chamber;
   a cold air duct connecting an evaporator with at least one cold air outlet hole formed in the cold air duct that is configured to discharge cold air generated by heat exchange in the evaporator to the storage chamber; and
   a sterilization device mounted at an upper surface of the storage chamber in order to sterilize and deodorize an interior of the storage chamber,
   wherein the sterilization device comprises
      a housing formed, at a front surface thereof, with an ion outlet while being formed, at a base surface thereof, with an air inlet;
      a blast unit mounted within the housing so as to suction air within the storage chamber to the air inlet and slantingly disposed in a direction of cold air discharged from a highest cold air outlet hole of the at least one cold air outlet hole formed in the cold air duct at a rear wall of the storage chamber;
      an ion generating unit mounted between the ion outlet and the blast unit so as to generate ions through supply of the air suctioned by the blast unit; and
      a guide portion formed at an inner side of the housing so as to guide the air discharged from the blast unit toward the ion generating unit,
      wherein the guide portion protrudes from the housing and includes an upwardly curved surface having predetermined curvature to reduce passage resistance of the air discharged from the blast unit, and a slanted surface to slant downwards toward the ion generating unit to accelerate air discharged to the ion outlet,
      wherein the blast unit is arranged adjacent to the highest cold air outlet hole so that the blast unit suctions only a partial portion of air discharged from the highest cold air outlet hole within the storage chamber, and
      wherein the entire blast unit is arranged above and inward of the highest cold air outlet hole.

2. The refrigerator according to claim 1, wherein the sterilization device is mounted in an attachable and detachable manner.

3. The refrigerator according to claim 1, wherein the blast unit is arranged within the housing to slant downwards toward the ion outlet.

4. The refrigerator according to claim 1, wherein the housing further comprises a shield portion which encases a circumference of the blast unit except for an ion outlet side.

5. The refrigerator according to claim 1, wherein the sterilization device further comprises a light emitting portion which displays an operation state of the sterilization device and a light penetrating member which transfers light emitted from the light emitting portion toward the ion outlet.

6. The refrigerator according to claim 1, wherein the sterilization device further comprises a deodorization filter to deodorize the air suctioned through the air inlet.

7. The refrigerator according to claim 2, further comprising a seizing portion provided at the upper surface of the storage chamber and a binding portion provided at the housing to allow the seizing portion to be coupled and seized,
   wherein the seizing portion and the binding portion are provided so as to be bound by contact therebetween during movement of the sterilization device along an upper wall of the storage chamber.

8. The refrigerator according to claim 2, wherein the storage chamber is provided, at the upper surface thereof, with a sterilization device mounting portion which is concavely formed upwards as a shape corresponding to the sterilization device, and the sterilization device is attachably mounted at the sterilization device mounting portion.

9. The refrigerator according to claim 1, further comprising:
   a door operation sensing portion to detect an opening and closing state of the door; and
   a control unit to control operation of the blast unit and ion generating unit depending on a signal detected from the door operation sensing portion.

10. The refrigerator according to claim 9, wherein:
    the sterilization device further comprises a drive circuit board which is electrically connected with the blast unit and the ion generating unit; and
    the drive circuit board turns ON/OFF the operation of the blast unit and ion generating unit depending on a control signal of the control unit.

11. The refrigerator according to claim 1, further comprising:
    a cold air circulating fan to circulate cold air which cools the storage chamber; and a control unit to control operation of the blast unit and ion generating unit depending on an operation signal of the cold air circulating fan.

\* \* \* \* \*